US010307063B2

(12) United States Patent
Lee et al.

(10) Patent No.: US 10,307,063 B2
(45) Date of Patent: Jun. 4, 2019

(54) OPTICAL MEASURING DEVICE AND ELECTRONIC DEVICE INCLUDING THE SAME

(71) Applicant: SAMSUNG ELECTRONICS CO., LTD., Suwon-si (KR)

(72) Inventors: Seung Jun Lee, Seoul (KR); Dong Ho Kim, Seoul (KR); Jung Mok Bae, Seoul (KR); Eui Seok Shin, Yongin-si (KR); Woo Chang Lee, Anyang-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 301 days.

(21) Appl. No.: 15/237,812

(22) Filed: Aug. 16, 2016

(65) Prior Publication Data

US 2017/0143209 A1    May 25, 2017

(30) Foreign Application Priority Data

Nov. 20, 2015 (KR) .................. 10-2015-0163602

(51) Int. Cl.
*A61B 5/00* (2006.01)
*A61B 5/1455* (2006.01)
(Continued)

(52) U.S. Cl.
CPC .......... *A61B 5/0059* (2013.01); *A61B 5/1455* (2013.01); *A61B 5/14532* (2013.01);
(Continued)

(58) Field of Classification Search
CPC .. A61B 5/0059; A61B 5/14532; A61B 5/1455
See application file for complete search history.

(56) References Cited

U.S. PATENT DOCUMENTS 5,190,857 A * 3/1993 Allen ................. G01N 21/6428
250/459.1
7,315,752 B2    1/2008 Kraemer et al.
(Continued)

FOREIGN PATENT DOCUMENTS

JP    2004294075 A    10/2004
JP    2005513491 A     5/2005
(Continued)

OTHER PUBLICATIONS

Kwon et al: "Development of Micro Variable Optics Array", MEMS, San Francisco, CA, USA, Jan. 26-30, 2014, pp. 72-75 (4 pages total).

*Primary Examiner* — Thaddeus B Cox
(74) *Attorney, Agent, or Firm* — Sughrue Mion, PLLC (57) ABSTRACT

An optical measuring device including a light source, a light beam path adjuster, a light detector and a controller is provided. The light source may emit light toward an object in a predetermined progress direction. The light beam path adjuster may be disposed between the light source and the object and may change a progress path of the light emitted from the light source. The light detector may receive the light that is reflected from the object after passing through the light beam path adjuster. The controller may compare a first effective beam path length of the reflected light that the light detector receives with a predetermined target beam path length and control a refractive angle of the light beam path adjuster based on a beam path length difference between the first effective beam path length and the predetermined target beam path length.

10 Claims, 7 Drawing Sheets

(51) Int. Cl.
*G01N 33/49* (2006.01)
*A61B 5/145* (2006.01)

(52) U.S. Cl.
CPC .............. *A61B 5/443* (2013.01); *A61B 5/681* (2013.01); *A61B 5/6803* (2013.01); *A61B 5/7278* (2013.01); *A61B 5/74* (2013.01); *G01N 33/49* (2013.01); *A61B 2562/0242* (2013.01)

(56) References Cited

U.S. PATENT DOCUMENTS

| | | | |
|---|---|---|---|
| 9,532,009 B1* | 12/2016 | Safai | G01B 11/00 |
| 2003/0233036 A1* | 12/2003 | Ansari | A61B 5/14532 600/316 |
| 2004/0068163 A1 | 4/2004 | Ruchti et al. | |
| 2008/0218696 A1* | 9/2008 | Mir | A61B 5/14532 351/219 |
| 2013/0155410 A1* | 6/2013 | Enderby | A61B 5/14532 356/445 |
| 2013/0201384 A1* | 8/2013 | Tsuji | G02B 3/14 348/345 |
| 2015/0045636 A1 | 2/2015 | Novotny et al. | |

FOREIGN PATENT DOCUMENTS

| | | | |
|---|---|---|---|
| JP | 2008104751 A | 5/2008 | |
| JP | 2009168670 A | 7/2009 | |
| JP | 2012191969 A | 10/2012 | |

\* cited by examiner

OPTICAL MEASURING DEVICE AND ELECTRONIC DEVICE INCLUDING THE SAME

CROSS-REFERENCE TO RELATED APPLICATION

This application claims priority from Korean Patent Application No. 10-2015-0163602, filed on Nov. 20, 2015 in the Korean Intellectual Property Office, the disclosure of which is incorporated herein by reference in its entirety.

BACKGROUND

1. Field

Apparatuses and methods consistent with exemplary embodiments relate to analyzing body component by using an optical measuring device.

2. Description of Related Art

An optical measurement method using infrared light or near infrared ray (NIR) may be used to measure a certain body component, such as blood sugar. By using the optical measurement method, a component in an object may be detected and/or analyzed in a non-invasive manner, or a diagnosis can be performed through the detection and/or the analysis. The optical measurement method includes a spectrum analysis method of detecting and/or analyzing a specific component by analyzing light absorptivity in a particular wavelength of transmitted light or reflected light spectrum, and the main example is a spectroscopic analysis method using a fourier transform infrared spectrometer (FTIR) large-scale spectroscopy.

In the spectrum analysis method, when measuring light emitted from a light source, for example a near infrared ray, is reflected from an object to be measured, and the reflected light is detected and analyzed. The reflected light includes light reflected from a surface as well as light passing through the object by a predetermined distance and reflected from the object. In the latter case, a predetermined distance that the measuring light passes through the object refers to an optical path length. Since the reflected light includes information on a component in the object when the measuring light passes through the object by an optical path length, the reflected light should have less noise to get accurate information, and the measuring light should sufficiently pass through the object by the optical length required for a measurement purpose. However, when the optical path length is excessively long, the intensity of the reflected light that a light detecting unit receives becomes weak, and a spectrum signal may be reduced, and thus it is preferable that the optical path length be stably maintained to suit a measurement purpose and/or a kind of component to be measured.

To this end, an optical measuring device capable of providing various optical path lengths is proposed. For example, a fiber probe including multiple light emitters or multiple light detectors may be used. The optical path length of the fiber probe can be adjusted by varying a distance between the light detector and the light emitter used for actual measurement.

Measurement of biometric information may be performed by a portable electronic device, such as a smart phone, or a wearable electronic device, such as a smart band, a smart watch and a smart glass. It is being concerned that the above-described optical measuring device is mounted to an electronic device as one of bio-related functions. Users can conveniently measure or analyze a subcutaneous component, such as a blood sugar, using the optical measuring device mounted on an electronic device regardless of time and place.

However, when the portable electronic device or wearable electronic device mounted with the optical measuring device is used, an interfacing status with the object (e.g., a skin) may vary depending on a user, and the interfacing status may also vary depending on a circumstance of the measurement (e.g., the position of skin in contact with the electronic device, a contact angle, contact tightness, and the like) even if the user is the same. For example, the position at which a smart watch is worn and the contact tightness between the smart watch and a skin generally vary depending on use every time a user wears the smart watch. Even if the smart watch is worn, an interfacing status between the smart watch and the skin may vary depending on time.

Therefore, when the optical measuring device is mounted on the portable electronic device or the wearable electronic device, it is important to ensure an optical path length to be a target beam path length according with a measurement purpose or a component and to uniformly maintain the optical path length every measurement.

SUMMARY

Exemplary embodiments address at least the above problems and/or disadvantages and other disadvantages not described above. Also, the exemplary embodiments are not required to overcome the disadvantages described above, and may not overcome any of the problems described above.

One or more exemplary embodiments provide an optical measuring device capable of ensuring a constant optical path length regardless of an interfacing status with an object to be measured, and an electronic device including the same.

Further, one or more exemplary embodiments provide an optical measuring device capable of adjusting an optical path length according to a kind of component to be measured or a measurement purpose, and an electronic device including the same.

Further still, one or more exemplary embodiments provide an optical measuring device capable of adjusting an optical path length and having a simple structure and a compact and slim size, and an electronic device including the same.

According to an aspect of an exemplary embodiment, there is provided the optical measuring device including a light source, a light beam path adjuster, a light detector and a controller. The light source may emit a light toward an object in a predetermined progress direction, and the light beam path adjuster may be disposed between the light source and the object, and may change a progress path of the light emitted from the light source. The light detector may receive the light that is reflected from the object after passing through the light beam path adjuster. The controller may compare a first effective beam path length of the reflected light that the light detector receives with a predetermined target beam path length and may control a refractive angle of the light beam path adjuster based on a beam path length difference between the first effective beam path length and the predetermined target beam path length.

According to an aspect of another exemplary embodiment, there is provided the optical measuring device including a light source, a light beam path adjuster, a light detector and a controller. The light source may emit a light toward an object in a predetermined progress direction, and the light beam path adjuster may be disposed between the light source and the object and may change a progress path of the light by changing a refractive angle of the light incident on a boundary surface between two immiscible liquids of the light beam path adjuster. The light detector may receive the light that is reflected from the object after passing through the light beam path adjuster. The controller may compare a first effective beam path length of the reflected light that the light detector receives with a predetermined target beam path length and may control the refractive angle of the light beam path adjuster based on a beam path length difference between the first effective beam path length and the predetermined target beam path length.

According to an aspect of another exemplary embodiment, there is provided a wearable electronic device including an optical measuring device configured to detect a light reflected from an object, and a bio-signal analyzer for analyzing a bio-signal using the detected light. The optical measuring device may include a light source, a light beam path adjuster a light detector and a controller. The light source may emit the light in a predetermined progress direction to be reflected from the object. The light beam path adjuster may change a progress path of the light incident by changing a refractive angle of the light incident on a boundary surface between two immiscible transparent liquids of the light beam path adjuster. The light detector may receive the light that is reflected from the object after passing through the light beam path adjuster. The controller may control a refractive angle of the light beam path adjuster based on a beam path length difference between a first effective beam path length of the reflected light and a predetermined target beam path length so that a second effective path length of a light, which is subsequently emitted from the light source and is received by the light detector, is within a predetermined range of the target beam path length.

BRIEF DESCRIPTION OF THE DRAWINGS

The above and/or other aspects will be more apparent by describing certain exemplary embodiments, with reference to the accompanying drawings, in which.

DETAILED DESCRIPTION

Exemplary embodiments are described in greater detail below with reference to the accompanying drawings.

In the following description and the drawings, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

Figure 1:
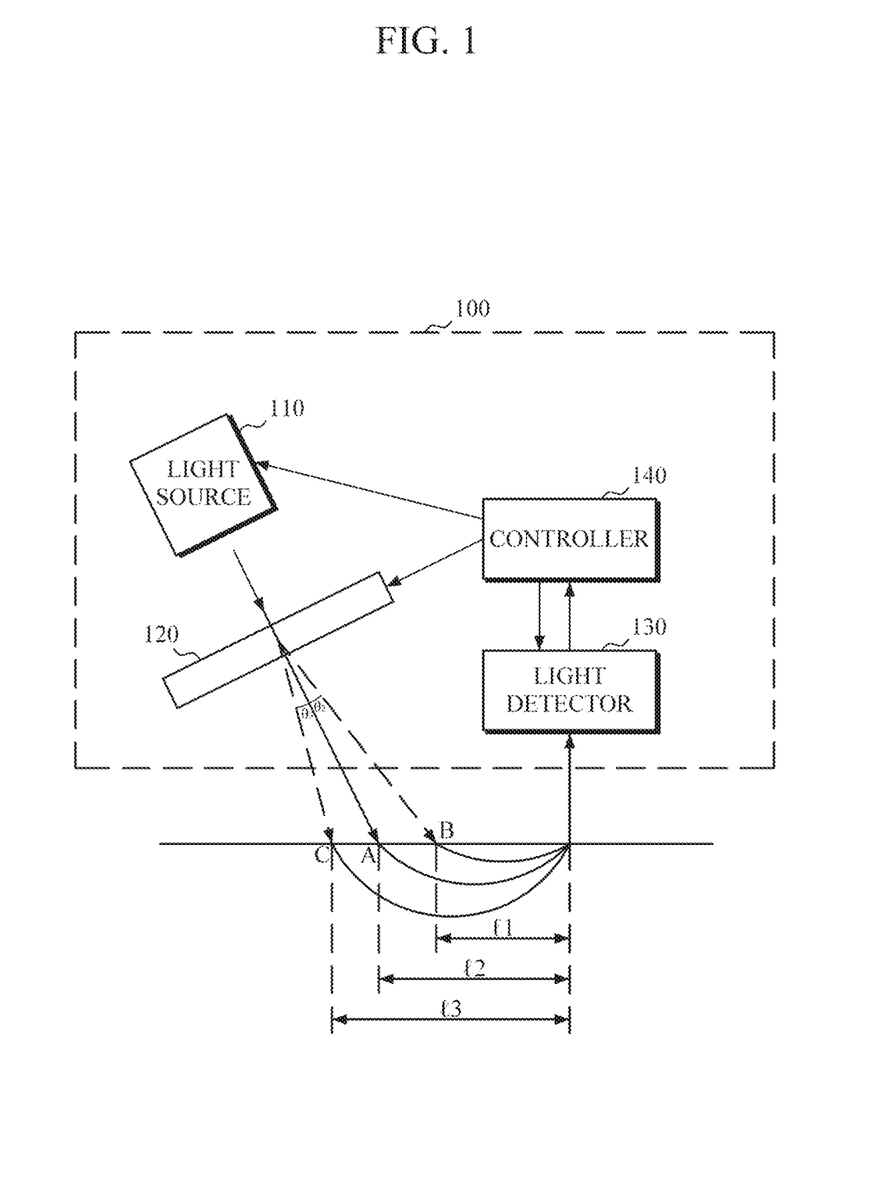
FIG. 1 is a block diagram showing a configuration of an optical measuring device according to an exemplary embodiment.

FIG. 1 is a block diagram showing a configuration of an optical measuring device according to an exemplary embodiment. Referring to FIG. 1, an optical measuring device 100 includes a light source 110, a light beam path adjuster 120, a light detector 130 and a controller 140.

The light source 110 emits measuring light according to a predetermined control signal. The control signal is generated by a controller 140 controlling an operation of the optical measuring device 100. The controller 140 may transmit the control signal to the light source 110. The light source 110 emits light with a predetermined wavelength, for example a near infrared ray (NIR), to perform measuring according to the control signal. However, the wavelength of the light emitted from the light source 110 may vary depending on a measurement purpose or a kind of component to be measured. It may not be necessary for the light source 110 to be configured of a single luminous body, and the light source 110 may be configured of a group of multiple luminous bodies. In the latter case, the multiple luminous bodies may emit light with wavelengths different from each other or light with the same wavelength to suit a measurement purpose.

For the measurement, the light source 110 emits the measuring light in a predetermined direction. That is, the direction in which the measuring light emitted from the light source 110 heads is uniform and is not changed during a predetermined time. For example, it is assumed that the measuring light goes straight by the light beam path adjuster 120 without refraction. In this case, when the optical measuring device 100, as shown in FIG. 1, is disposed to be parallel to an object to be measured, the measuring light from the light source 110 is incident on a light source interfacing point A of the object. However, when the optical measuring device 100 is not disposed to be parallel to the object and slantingly faces the object in one direction, the light source interfacing point may be a point B or a point C rather than the point A.

However, the direction of the measuring light emitted from the light source 110 does not necessarily have to be fixed permanently. For example, the optical measuring device 100 may include a component configured to change the direction of light output from the light source 110. When an additional operation from the outside of the optical measuring device 100 is performed by a user, or a measurement purpose or a kind of component to be measured is changed, the component configured to change the direction of light output from the light source 110 may be additionally provided in the light source 110.

The light beam path adjuster 120 may change a progress path of the measuring light emitted from the light source 110 in a predetermined direction and incident on the object. More specifically, the light beam path adjuster 120 may pass the measuring light in a first direction in an initial state. In addition, the light beam path adjuster 120 may allow the measuring light to travel in a different direction rather than the first direction according to a control from the controller 140.

When the light beam path adjuster 120 does not receive the control signal from the controller 140 (e.g., an initial state of the light measuring device 100), the light beam path adjuster 120 allows the measuring light emitted from the light source 110 to travel straight and to be incident on the light source interfacing point A of the object. The light beam path adjuster 120 may change the progress direction so that the measuring light is incident on a random point (e.g., the point B or C) other than the light source interfacing point A according to the control signal from the controller 140. An operation control of the light beam path adjuster 120 by the controller 140 will be described below in detail.

As a method for changing a progress direction, the light beam path adjuster 120 may allow the measuring light to be incident on another point of the object by refracting the measuring light at a predetermined angle. According to this, the refractive angle is changed by the light beam path adjuster 120 according to the control signal from the controller 140, and thus the progress direction of the measuring light passing through the light beam path adjuster 120 may be changed. For example, the refractive angle by the light beam path adjuster 120 may be 0°. In this case, the measuring light may travel straight to the light source interfacing point A of the object without changing the progress path of the measuring light. The refractive angle by the light beam path adjuster 120 may be $\theta2$ or $-\theta3$. In this case, the progress direction of the measuring light is changed, and the measuring light may be incident on the point B or C other than the light source interfacing point A.

Figure 2:
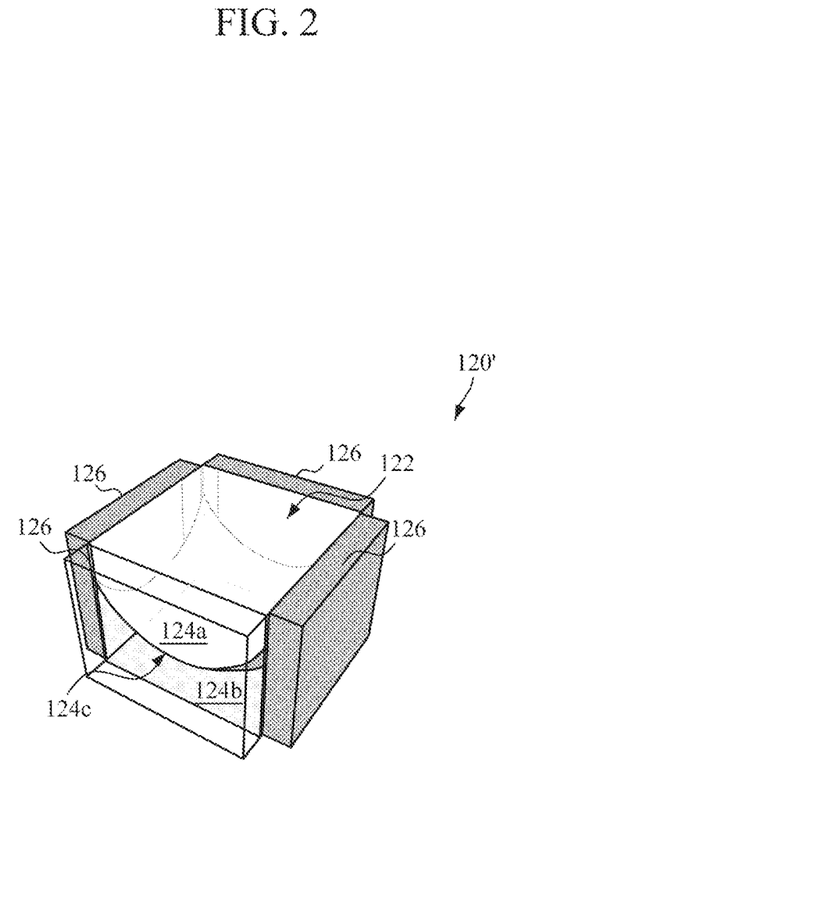
FIG. 2 is a perspective view schematically showing a micro variable optics.

FIG. 2 is a perspective view schematically showing a micro variable optics 120' as an example of the light beam path adjuster 120 operated in a method of changing a refractive angle of the measuring light. Referring to FIG. 2, the micro variable optics 120' includes a container 122, two immiscible liquids 124a and 124b contained in the container 122, and electrodes 126. The light beam path adjuster 120 may include a single micro variable optics 120' or an array of a plurality of micro variable optics 120'.

The container 122 may accommodate the two liquids 124a and 124b. The size of the container 122 is not particularly limited, but may have a micro scale. The container 122 is formed of a transparent material as a whole, or at least a surface (e.g., an upper surface and a lower surface in FIG. 2) used in a direction in which the measuring light is input and output may be formed of a transparent material. A dielectric layer may be coated with a single layer or multiple layers formed of a dielectric material so that an inner surface of the container 122, i.e., a surface on which the two liquids 124a and 124b are in contact with each other (at least four inner surfaces of side walls), uses electro-wetting properties. The dielectric material may be Teflon, parylene, SiNx and the like, but is not limited thereto.

The two liquids 124a and 124b are two immiscible liquids. Therefore, a boundary surface 124c is present between the two liquids 124a and 124b accommodated in the container 122. The direction of the boundary surface 124c may be changed depending on the shape of the container 122. The measuring light may pass while maintaining an incident angle of the light or may be refracted at a predetermined angle depending on the direction of the boundary surface 124c for the direction in which the measuring light is incident, and thus the boundary surface 124c functions as a refractive surface of the measuring light.

One of the two liquids 124a and 124b is a conductive liquid, and the other one is an insulating liquid. As an example, a first liquid 124a positioned at an upper side of the two liquids 124a and 124b may be the conductive liquid, and a second liquid 124b positioned at a lower side of the two liquids 124a and 124b may be the insulating liquid. However, this is exemplary, and it is apparent that the electrical properties of the two liquids 124a and 124b may be opposite thereto.

The conductive liquid may be pure water or water containing a predetermined electrolyte. The insulating liquid may be oil. However, the present exemplary embodiment is not limited thereto, and a type used as a conductive liquid or an insulating liquid is not particularly limited. However, it will be more useful to use a liquid capable of precisely controlling a spreading degree using an electro-wetting phenomenon to be described below as the conductive liquid.

A plurality of electrodes 126 are provided on an external wall of the container 122. Alternatively, the plurality of electrodes 126, more specifically a plurality of electrodes 126 with inner surfaces coated with dielectric layers, may function as a part of the container 122 (four side walls constituting the container 122 in FIG. 2). The plurality of electrodes 126 may be configured to allow voltages to be applied independently. FIG. 2 shows that the four electrodes 126 are respectively provided at side walls of the hexahedral container 122 or function as side walls. But this is exemplary, and more electrodes may be provided, or an electrode may be additionally provided at a different position other than a side wall.

The plurality of electrodes 126 may use an electro-wetting phenomenon of the conductive liquid 124a of the two liquids 124a and 124b. When predetermined voltages are applied to the plurality of electrodes 126 respectively according to the electro-wetting phenomenon to generate an electric field in the container 122, the spreading degree of the conductive liquid 124a, that is, the spreading degree for an internal wall of the container 122, is changed. When the intensity or direction of the applied voltage is changed, a degree of change in spreading or the direction of change can be controlled.

Like this, when the spreading of the conductive liquid 124a is changed, an area in which the conductive liquid 124a is distributed is changed, and thus the space of the container 122 occupied by each of the two liquids 124a and 124b is changed. Accordingly, the direction of the boundary surface 124c between the two liquids 124a and 124b may be changed. Ultimately, it is possible to change the direction of the boundary surface 124c by adjusting the voltages applied to the electrodes 126. Also, as the direction of the boundary surface 124c is precisely controlled, the boundary surface 124c may allow a continuous refractive interface for the measuring light to be formed.

Figure 3A:
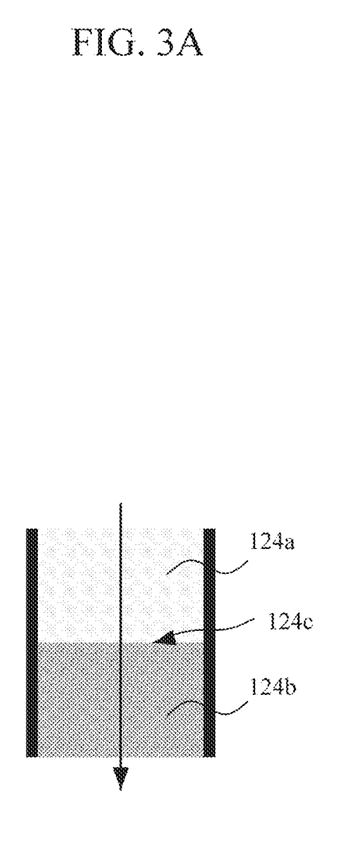
FIGS. 3A, 3B, and 3C are views schematically showing a principle to adjust a refractive angle of measuring light using the micro variable optics.
Figure 3B:
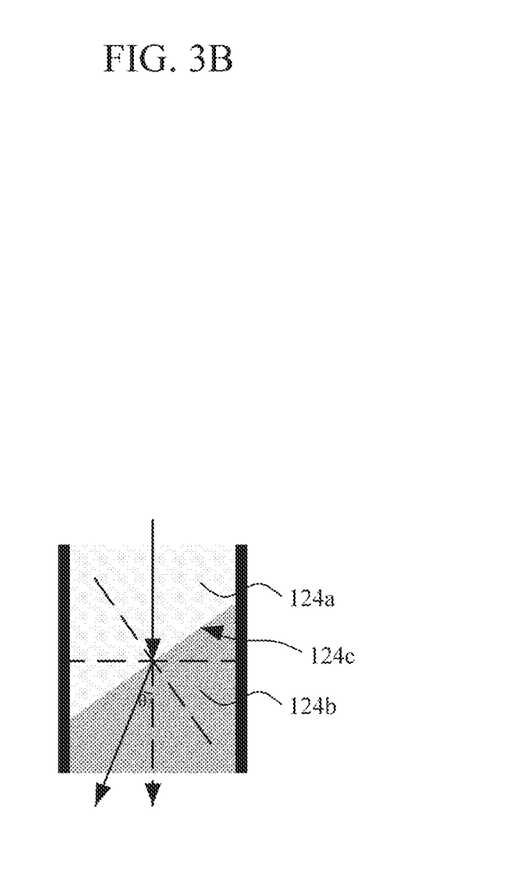
Figure 3C:
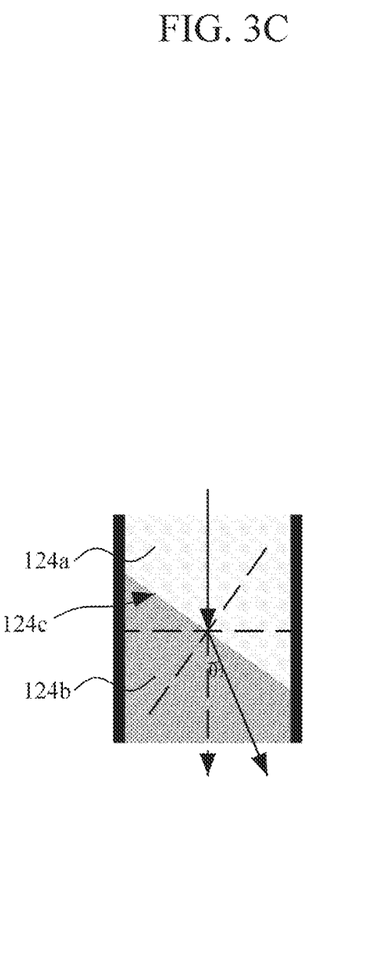

FIGS. 3A, 3B, and 3C are views schematically showing a principle to adjust a refractive angle of the measuring light using the micro variable optics 120' shown in FIG. 2 or an array thereof. In FIGS. 3A to 3C, reference numbers 124a and 124b correspond to the first liquid and the second liquid in FIG. 2, respectively, and a reference number 124c represents a boundary surface between the two liquids 124a and 124b. According to FIGS. 3A to 3C, the boundary surfaces 124c in respective drawings are different from each other. When the intensity and/or the direction of an electric field generated in the container 122 is changed, the boundary surface 124c may be changed according to the electro-wetting phenomenon of the conductive liquid 124a as described above.

First, referring to FIG. 3A, the incident measuring light travels straight without refraction on the horizontal boundary surface 124c and is output from the micro variable optics. Referring to 3B, when the direction of the boundary surface 124c is changed to the upper right (i.e., when the incline angle of the boundary surface 124c is changed so that the right end of the boundary surface 124c is positioned higher than the left end of the boundary surface 124c), the incident measuring light is also refracted to the left from the boundary surface 124c at a predetermined angle $\theta3$ and is output from the micro variable optics. Referring to 3C, when the direction of the boundary surface 124c is changed to the lower right (i.e., when the incline angle of the boundary surface 124c is changed so that the right end of the boundary surface 124c is positioned lower than the left end of the boundary surface 124c), the incident measuring light is also refracted to the right from the boundary surface 124c at a predetermined angle θ2 and is output from the micro variable optics.

When the light beam path adjuster 120 is only electrically driven and does not additionally require a hardware driving component like the micro variable optics 120' shown in FIG. 2, the light beam path adjuster 120 may be manufactured to be smaller and thinner, thereby being easily mounted as one module of a portable electronic device, a wearable electronic device, or the like. When the maximum refractive angle of the micro variable optics 120' shown in FIG. 3B or 3C, (i.e., the maximum range in which the progress direction is adjustable) is 15°, and the measuring light is incident on a point which is maximum 0.2 mm away from the light source interfacing point A (see FIG. 1), the height required for the micro variable optics 120' may be about 0.74 mm. According to this, the optical measuring device 100 may be manufactured at a small thickness of about 1 mm as a whole.

The light beam path adjuster 120 in FIG. 1 is not limited to the micro variable optics 120' shown in FIG. 2 and may be variously implemented when the progress path of the incident measuring light is adjustable. For example, the light beam path adjuster 120 may include a combination of reflectors in which at least one reflective angle is adjustable and a driver capable of driving (changing a reflective angle by the reflector) at least one reflector. As another example, the light beam path adjuster 120 may include a refractive device with a predetermined refractive angle and an adjuster capable of adjusting (e.g., axially rotating) the refractive device so that the direction of refraction by the refractive device is changed.

For another example, the light beam path adjuster 120 may include a liquid crystal capable of changing a beam path by allowing the refractive index to be changed depending on the intensity of electric field, and a driving electrode for generating an electric field on the liquid crystal.

The light detector 130 receives the reflected light of the measuring light passing through the light beam path adjuster 120 and reflected from an object to be measured. In this case, the reflected light is not limited to the measuring light which is incident and reflected from the surface of the object, and transmitted light substantially passing through the object at a predetermined distance is also included in the reflected light. Because the transmitted light contains information on the inside of the object, the transmitted light may be utilized to analyze a component in the object and the like such as a blood sugar.

The light detector 130 is disposed to be apart from the light source 110 by a predetermined distance. That is, a distance between the light detector 130 and the light source 110 may not be changed. Therefore, an effective beam path length that is a length in which the measuring light passes through the object may be changed depending on where a point of the object at which the measuring light is incident from the light source 110 is. As described above, when a certain progress path of the measuring light is set by the light beam path adjuster 120, a point of the object at which the measuring light is incident may be changed depending on an interfacing status between the optical measuring device 100 and the object. Therefore, the effective beam path length of the reflected light may be changed depending on an interfacing status between the optical measuring device 100 and the object.

The effective beam path length of the reflected light received by the light detector 130 may be calculated. The effective beam path length may be calculated using known various methods and is not particularly limited. For example, the effective beam path length passing through the object, for example a water component in a skin, may be calculated using a known classical least square (CLS) method. The calculation of the effective beam path length may be performed by the light detector 130 or by other units constituting the controller 140 or the optical measuring device 100.

The reflected light received by the light detector 130 may be utilized to analyze a component (e.g., a blood sugar) in the object. That is, the reflected light that the light detector 130 receives may be utilized to analyze a component in the object through a known method such as a spectrum analysis method. To this end, the optical measuring device 100 may additionally include a spectrum analyzer. The analyzer may be also implemented as one function of the light detector 130 or the controller 140 or as other unit of the optical measuring device 100.

A function of diagnosing based on a final result by the analyzer, such as a measured value for a component, or the measured value may be implemented as one function of the analyzer. Alternatively, a function of obtaining a final measured value or diagnosing based on the final measured value may be implemented as one function of an electronic device in which the optical measuring device 100 is installed. For example, the function may be implemented as one function of an operating system (OS) of a mobile electronic device or a wearable electronic device in which the optical measuring device 100 is installed and/or a function of a specific application installed in the electronic device.

Referring to FIG. 1, the controller 140 controls the operation of the light beam path adjuster 120 in a feedback method using the effective beam path length of the reflected light that the light detector 130 receives. For example, the controller 140 compares the effective beam path length (hereinafter, referred to as a first effective beam path length) of the reflected light that the light detector 130 receives with a predetermined target beam path length and may control an operation of the light beam path adjuster 120 so that the effective beam path length (hereinafter, referred to as a second effective beam path length) of the reflected light by the following measuring light corresponds to a target beam path length It.

In this case, as described above that, the effective beam path length refers to a distance in which the measuring light substantially passes through the object. In FIG. 1, when the light beam path adjuster 120 is controlled by the controller 140 so that the measuring light travels straight while maintaining an incident angle of the measuring light, the effective beam path length becomes l1. When the light beam path adjuster 120 is controlled by the controller 140 so that the measuring light is refracted by θ2, the effective beam path length becomes l2. When the light beam path adjuster 120 is controlled by the controller 140 so that the measuring light is refracted by −θ3, the effective beam path length becomes l3.

The target beam path length It refers to a predetermined distance in which the measuring light should pass through the object to achieve a measurement purpose. Therefore, the target beam path length It may vary depending on a measurement purpose or a kind of component to be measured, but a specific value may be determined in advance.

To control the light beam path adjuster 120, first, the controller 140 sets the light beam path adjuster 120 to be in an initial state and allows the first measuring light to pass. For example, the controller 140 sets the light beam path adjuster 120 to be in a state in which the measuring light travels straight while maintaining its incident angle (i.e., a state in which the refractive angle is 0° as an initial state), or in a state in which any driving power is not applied to the light beam path adjuster 120, for example a state in which any voltage is not applied to the electrodes 126 in FIG. 2, as an initial state. However, this is exemplary, and a state in which the refractive angle of the light beam path adjuster 120 has a predetermined angle or a state in which predetermined driving power is applied to the light beam path adjuster 120 may be an initial state. Hereinafter, the description of the controller 140 will be continued on the assumption that a state in which the measuring light goes straight is an initial state because any driving power is not applied to the light beam path adjuster 120.

The controller 140 compares the effective beam path length I1 of the first reflected light, that is, the first effective beam path length, with the predetermined target beam path length It and controls an operation of the light beam path adjuster 120 depending on a value determined based on a comparison result. As an example, the controller 140 compares whether the first effective beam path length I1 corresponds to the target beam path length It, and when the two values do not correspond to each other, the controller 140 may control an operation of the light beam path adjuster 120 so that the second effective beam path length corresponds to the target beam path length It. In this case, the meaning that 'the two values correspond to each other' is not limited to that the values are exactly equal, and generally includes that a difference between the two values is within a predetermined range, for example, a range in which a component is easily analyzed using the reflected light, in an allowable range.

In this case, a beam path adjusting value by the light beam path adjuster 120, that is, how long and in which direction a beam path is adjusted, may be determined depending on a predetermined algorism based on a difference between the first effective beam path length I1 and the target beam path length It, that is, a beam path length difference. More specifically, when the beam path length difference I1−It is a predetermined negative number, for example I1−I3, a beam path adjusting value by the light beam path adjuster 120 is a refractive angle of −θ3, and the second effective beam path length may be greater than the first effective beam path length by the beam path length difference I3−I1. In this case, the second measuring light may be incident on the point C. Also, when the beam path length difference I1−It is a predetermined positive number, for example I1−I2, the beam path adjusting value by the light beam path adjuster 120 is a refractive angle of θ2, and the second effective beam path length may be smaller than the first effective beam path length by the beam path length difference I1−I2. In this case, the second measuring light may be incident on the point B.

The light beam path adjuster 120 may be controlled by the controller 140 only when the beam path length difference that is a difference between the first effective beam path length I1 and the target beam path length It is less than a predetermined threshold. More specifically, when the beam path length difference is less than the threshold, the controller 140, as described above, controls the light beam path adjuster 120 so that the second effective beam path length becomes the same as the target beam path length.

On the other hand, when the beam path length difference is greater than the threshold, the controller 140 does not control an operation of the light beam path adjuster 120. Because, in this case, the beam path length difference is too large so that it is impossible for the second effective beam path length to become the same as the target beam path length It even if the progress path of the measuring light is maximally adjusted using the light beam path adjuster 120, or the beam path adjusting value is too large, and the progress path is too changed, and thus the sufficient intensity of the reflected light is not detected by the light detector 130. Therefore, it is not valuable to control the light beam path adjuster 120 again.

In this case, the controller 140 may allow an immeasurability notice message that indicates that measurement is impossible to be output. A kind or a form of the immeasurability notice message is not particularly limited. For example, the immeasurability notice message may be a notice message or a warning message to simply indicate that measurement is impossible and/or a request message that requests a user to perform measurement again. As an example of the latter case, when the optical measuring device 100 is a component of a portable electronic device, the immeasurability notice message may be a re-measurement request message that requests re-measurement by changing an interfacing status between the portable electronic device and the object. As another example of the latter case, when the optical measuring device 100 is one component of a wearable electronic device, the immeasurability notice message may be a re-wear request message that requests to wear the wearable electronic device again.

Figure 4:
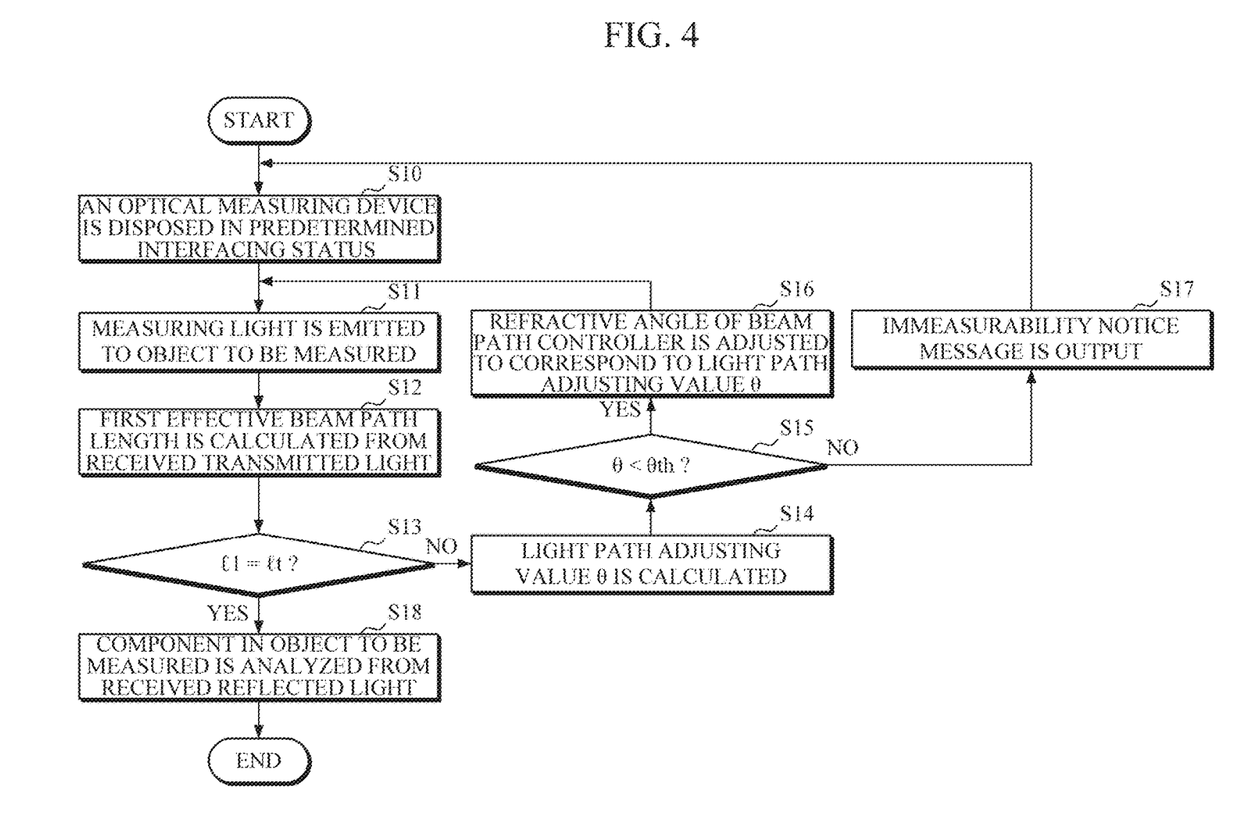
FIG. 4 is a flowchart showing an example of a measuring process using the optical measuring device of FIG. 1.

Next, a measurement procedure that performs measurement will be described using the optical measuring device 100 in FIG. 1. FIG. 4 is a flowchart showing an example of the measurement procedure.

Referring to FIGS. 1 to 4, the optical measuring device 100 is disposed to be in a certain interfacing status with respect to the object (operation S10). For example, when the optical measuring device 100 is one component of a portable electronic device, a user may dispose a portion of the optical measuring device 100 of the portable electronic device to be adjacent to or to be in contact with the object. Alternatively, when the optical measuring device 100 is one component of a wearable electronic device, the user may wear the wearable electronic device at a predetermined position such as a wrist, for example, in the case of a smart watch, or eyes, for example in the case of a smart glass.

The first measuring light is discharged from the light source 110 of the optical measuring device 100 to emit the measuring light to the object (operation S11). In this case, the light beam path adjuster 120 allows the measuring light to travel straight from the light source 110 to be incident on the light source interfacing point A of the object, but this is exemplary as described above. The optical measuring device 100 receives the first reflected light caused by the first measuring light through the light detector 130 and obtains the first effective beam path length I1 through a spectrum analysis for the received first reflected light (operation S12).

Then, the optical measuring device 100 determines whether the effective beam path length I1 obtained in operation S12 corresponds to the target beam path length It (operation S13). In this case, the meaning that the two values correspond to each other is not limited to that the values are exactly equal, and includes that a difference between the two values is within an allowable range. When it is determined that the effective beam path length I1 corresponds to the target beam path length It in operation S13, the optical measuring device 100 analyzes a component in the object (e.g., a blood sugar in a subcutaneous tissue) through the spectrum analysis and the like for the first reflected light (operation S18).

Whereas, as a result of the determination in operation S13, when the effective beam path length I1 does not correspond to the target beam path length It, the optical measuring device 100 calculates a beam path adjusting value θ showing a size of the beam path to be adjusted by the light beam path adjuster 120 (operation S14). The calculated beam path adjusting value θ and a predetermined threshold θth are compared in size (operation S15). As a result of the comparison, when the beam path adjusting value θ is less than the predetermined threshold θth, the refractive angle of the light beam path adjuster 120 is controlled to correspond to the beam path adjusting value θ calculated in operation S14. Subsequently, the second measuring light is emitted to the object, and the processes after operation S11 are repeated. If necessary, the processes may be repeated twice or more until the effective beam path length I1 corresponds to the target beam path length It.

Whereas, as a result of the comparison in operation of S15, when the beam path adjusting value θ is greater than the predetermined threshold θth, the optical measuring device 100 outputs an immeasurability notice message (e.g., a re-measurement request message or a re-wear request message indicating to change an interfacing status between the optical measuring device 100 and the object). When the immeasurability notice message is output, the user may put the portable electronic device to the object again or wear the wearable electronic device again so that the interfacing status between the optical measuring device 100 and the object is changed.

Figure 5:
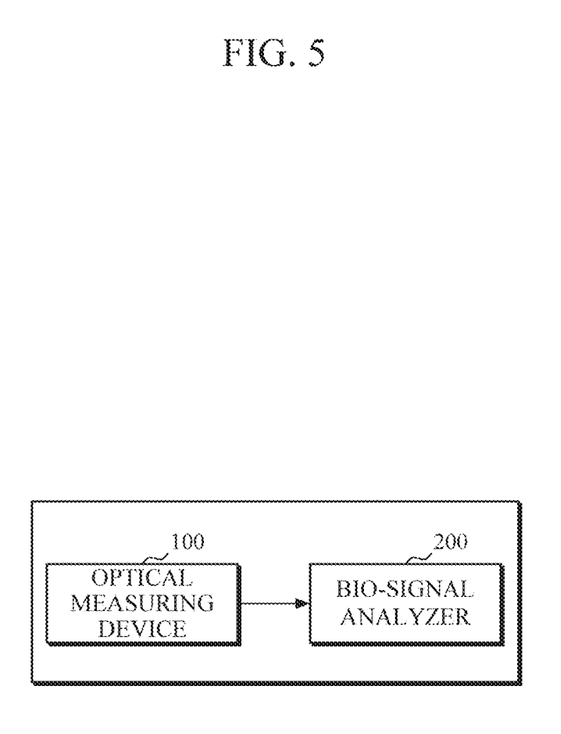
FIG. 5 is a block diagram schematically showing an example of a configuration of an electronic device according to the exemplary embodiment.

FIG. 5 is a block diagram schematically showing an example of a configuration of the electronic device including the optical measuring device 100 in FIG. 1. The electronic device shown in FIG. 5 may be a portable electronic device or a wearable electronic device, but is not limited thereto. Referring to FIG. 5, the electronic device includes the optical measuring device 100 and a bio-signal analyzer 200, and the optical measuring device 100 is described above in detail with reference to FIGS. 1 to 4. Therefore, the detailed description thereof will be omitted.

The bio-signal analyzer 200 analyzes a bio-signal, such as a blood sugar, using the result of measurement measured by the optical measuring device 100. Here, the result of the measurement measured by the optical measuring device 100 is data measured in a state, that is, operation S18 in FIG. 4, in which the effective beam path length corresponds to the target beam path length according to the measurement method described with reference to FIG. 4. Therefore, the result of measurement is data obtained by analyzing the first reflected light or data obtained by analyzing the second reflected light received by controlling the refractive angle to a predetermined refractive angle based on the effective beam path length of the first reflected light by the light beam path adjuster. The result of measurement may be spectrum analysis data for the received reflected light.

While not restricted thereto, the operations or steps of the methods or algorithms according to the above exemplary embodiments may be embodied as computer-readable codes on a computer-readable recording medium. The computer-readable recording medium may be any recording apparatus capable of storing data that is read by a computer system. Examples of the computer-readable recording medium include read-only memories (ROMs), random-access memories (RAMs), CD-ROMs, magnetic tapes, floppy disks, and optical data storage devices. The computer-readable recording medium may be a carrier wave that transmits data via the Internet, for example. The computer-readable medium may be distributed among computer systems that are interconnected through a network so that the computer-readable code is stored and executed in a distributed fashion. Also, the operations or steps of the methods or algorithms according to the above exemplary embodiments may be written as a computer program transmitted over a computer-readable transmission medium, such as a carrier wave, and received and implemented in general-use or special-purpose digital computers that execute the programs. Moreover, it is understood that in exemplary embodiments, one or more units of the above-described apparatuses and devices can include or implemented by circuitry, a processor, a microprocessor, etc., and may execute a computer program stored in a computer-readable medium.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An optical measuring device comprising:
a light source configured to emit light toward an object in a predetermined progress direction;
a light beam path adjuster that is configured to be disposed between the light source and the object and change a progress path of the light emitted from the light source;
a light detector configured to receive the light that is emitted to and reflected from the object after passing through the light beam path adjuster; and
a controller configured to compare a first effective beam path length of the light that the light detector receives with a predetermined target beam path length and control a refractive angle of the light beam path adjuster based on a beam path length difference between the first effective beam path length and the predetermined target beam path length.

2. The optical measuring device of claim 1, wherein the controller is further configured to control the refractive angle of the light beam path adjuster according to a beam path adjusting value determined based on the beam path length difference, so that a second effective beam path length of light, which is subsequently emitted from the light source and is received by the light detector, is within a predetermined range of the predetermined target beam path length.

3. The optical measuring device of claim 2, wherein the controller is further configured to determine the beam path adjusting value from the beam path length difference using a predetermined algorithm.

4. The optical measuring device of claim 2, wherein the controller is further configured to determine the beam path adjusting value using a database in which the beam path adjusting value corresponding to the beam path length difference is determined.

5. The optical measuring device of claim 2, wherein the controller is further configured to control the refractive angle of the light beam path adjuster only when the beam path length difference or the beam path adjusting value is less than a predetermined threshold.

6. The optical measuring device of claim 5, wherein the controller is further configured to output an immeasurability notice message indicating that measurement is impossible in response to the beam path length difference or the beam path adjusting value being greater than the predetermined threshold.

7. The optical measuring device of claim 1, wherein the light beam path adjuster is further configured to change the progress path using two immiscible liquids to form a continuous refractive interface.

8. The optical measuring device of claim 7, wherein the light beam path adjuster comprises:
 two immiscible fluids which are accommodated in one container to form a boundary surface; and
 a refractive angle adjuster configured to adjust the refractive angle by changing an incline angle of the boundary surface to which the light is incident.

9. The optical measuring device of claim 8, wherein the two immiscible fluids respectively correspond to a conductive fluid and an insulating fluid, and
 the refractive angle adjuster comprises a plurality of electrodes generating a predetermined size of electric field in the container so that the incline angle of the boundary surface is changed according to an electro-wetting property of the conductive fluid.

10. The optical measuring device of claim 1, wherein the predetermined progress direction of the light emitted from the light source is constant, and
 the light detector is disposed apart from the light source by a predetermined distance.

\* \* \* \* \*